(12) United States Patent
Kolata et al.

(10) Patent No.: US 7,037,305 B2
(45) Date of Patent: May 2, 2006

(54) HEART PRESENTATION DEVICE AND METHOD

(75) Inventors: Ronald J. Kolata, Cincinnati, OH (US); Michael F. Clem, Maineville, OH (US); Christopher J. Hess, Lebanon, OH (US); Gary W. Knight, West Chester, OH (US); Kristin L. Jambor, Cincinnati, OH (US); David L. Hamann, Cincinnati, OH (US)

(73) Assignee: Ethicon, Inc., Somerville, NJ (US)

( * ) Notice: Subject to any disclaimer, the term of this patent is extended or adjusted under 35 U.S.C. 154(b) by 40 days.

(21) Appl. No.: 09/845,898

(22) Filed: Apr. 30, 2001

(65) Prior Publication Data

US 2003/0167055 A1    Sep. 4, 2003

(51) Int. Cl.
*A61B 17/00* (2006.01)
(52) U.S. Cl. .......................................................... 606/1
(58) Field of Classification Search .................... 606/1, 606/205–209, 210–211, 216–221, 75, 116, 606/117, 118, 120, 151, 157, 188, 122, 142; 128/898; 132/273, 275, 276, 277; 40/300, 40/301, 302; 294/19.1, 19.2, 50.8, 100, 97, 294/115
See application file for complete search history.

(56) References Cited

U.S. PATENT DOCUMENTS

| | | | | |
|---|---|---|---|---|
| 273,243 A * | 3/1883 | Adams | ...................... | 294/115 |
| 276,658 A * | 5/1883 | Betts | ........................... | 294/1.1 |
| 406,546 A * | 7/1889 | Taber | ........................ | 294/19.3 |
| 443,689 A * | 12/1890 | Welke | ..................... | 294/86.28 |
| 525,076 A * | 8/1894 | Heffner | ....................... | 294/115 |
| 658,392 A * | 9/1900 | Patton | ............................ | 7/170 |
| 746,455 A * | 12/1903 | Campbell | ................... | 294/19.3 |
| 1,056,343 A * | 3/1913 | Kromann | .................... | 294/19.3 |
| 1,171,315 A * | 2/1916 | Bryant | ..................... | 294/86.27 |
| 1,534,954 A * | 4/1925 | Holtz | ......................... | 294/19.3 |
| 1,967,731 A * | 7/1934 | Ackerson | ..................... | 294/115 |
| 2,136,661 A * | 11/1938 | Branson | ..................... | 294/19.3 |
| 2,195,832 A * | 4/1940 | Wagenhauser | ............. | 269/54.3 |
| 2,196,117 A * | 4/1940 | Lange | ........................ | 294/19.3 |
| 2,411,944 A * | 12/1946 | Stone | ......................... | 606/116 |
| 3,783,873 A * | 1/1974 | Jacobs | ........................ | 128/303 |
| 3,826,160 A * | 7/1974 | Allen et al. | .................... | 29/238 |
| 3,951,138 A | 4/1976 | Akopov | ........................ | 128/17 |
| 3,999,555 A * | 12/1976 | Person | ........................ | 607/130 |
| 4,522,206 A * | 6/1985 | Whipple et al. | ............ | 128/312 |
| 5,074,870 A * | 12/1991 | von Zeppelin | .............. | 606/158 |
| 5,119,585 A * | 6/1992 | Camp | ......................... | 43/53.5 |
| 5,141,514 A * | 8/1992 | van Amelsfort | ............ | 606/117 |
| 5,201,739 A * | 4/1993 | Semm | ......................... | 606/106 |
| 5,275,615 A * | 1/1994 | Rose | .......................... | 606/208 |
| 5,308,358 A * | 5/1994 | Bond et al. | ................. | 606/205 |

(Continued)

*Primary Examiner*—Eduardo C. Robert
*Assistant Examiner*—Anu Ramana
(74) *Attorney, Agent, or Firm*—Nutter, McClennen & Fish LLP (57) ABSTRACT

A medical instrument for positioning an internal organ during surgical and diagnostic procedures is provided. In one embodiment, the medical instrument includes a body having a tissue grasping element and an actuating member effective to move the tissue grasping element between an open position and a closed position. The body also includes a flexible member which has a portion secured to the body and at least one free end. In use, the tissue grasping element grasps or penetrates a portion of the tissue on or near the body organ. Tension can then be applied to the flexible member to reposition and secure the body organ.

21 Claims, 8 Drawing Sheets

U.S. PATENT DOCUMENTS

| | | | |
|---|---|---|---|
| 5,362,294 A * | 11/1994 | Seitzinger | 600/37 |
| 5,368,596 A * | 11/1994 | Burkhart | 606/79 |
| 5,407,243 A * | 4/1995 | Riemann | 294/100 |
| 5,415,160 A | 5/1995 | Ortiz et al. | 128/20 |
| 5,474,057 A * | 12/1995 | Makower et al. | 600/214 |
| 5,507,796 A | 4/1996 | Hasson | 606/148 |
| 5,540,237 A | 7/1996 | Mers Kelly | 128/845 |
| 5,540,648 A | 7/1996 | Yoon | 600/114 |
| 5,562,447 A * | 10/1996 | Moy et al. | 433/150 |
| 5,569,274 A * | 10/1996 | Rapacki et al. | 606/158 |
| 5,591,203 A * | 1/1997 | Fahy | 606/207 |
| 5,667,526 A * | 9/1997 | Levin | 606/207 |
| 5,674,228 A * | 10/1997 | Henderson et al. | 606/137 |
| 5,702,352 A | 12/1997 | Kimura et al. | 600/201 |
| 5,713,910 A | 2/1998 | Gordon et al. | 606/144 |
| 5,718,714 A * | 2/1998 | Livneh | 606/205 |
| 5,782,748 A * | 7/1998 | Palmer et al. | 600/104 |
| 5,817,119 A * | 10/1998 | Klieman et al. | 606/174 |
| 5,826,928 A * | 10/1998 | Shang | 294/24 |
| 5,832,651 A * | 11/1998 | Arntz | 43/5 |
| 5,893,878 A * | 4/1999 | Pierce | 606/207 |
| 5,921,979 A * | 7/1999 | Kovac et al. | 606/1 |
| 5,944,729 A * | 8/1999 | Blake | 606/139 |
| 5,954,057 A | 9/1999 | Li | 128/898 |
| 5,972,021 A * | 10/1999 | Huttner et al. | 606/210 |
| 5,997,545 A * | 12/1999 | Doherty et al. | 606/102 |
| 6,001,120 A * | 12/1999 | Levin | 606/207 |
| 6,015,382 A | 1/2000 | Zwart et al. | 600/207 |
| 6,050,996 A * | 4/2000 | Schmaltz et al. | 606/51 |
| 6,090,129 A * | 7/2000 | Ouchi | 606/206 |
| 6,106,041 A * | 8/2000 | Eckhardt | 294/99.2 |
| 6,126,665 A | 10/2000 | Yoon | 606/144 |
| 6,132,370 A | 10/2000 | Furnish et al. | 600/235 |
| 6,228,023 B1 * | 5/2001 | Zaslavsky et al. | 600/204 |
| 6,256,923 B1 * | 7/2001 | Norton | 43/4 |
| 6,520,556 B1 * | 2/2003 | Hsu | 294/19.1 |
| 6,585,643 B1 * | 7/2003 | Clem et al. | 600/210 |
| 6,813,976 B1 * | 11/2004 | Malvini et al. | 81/300 |

* cited by examiner

HEART PRESENTATION DEVICE AND METHOD

FIELD OF THE INVENTION

The present invention relates to methods and apparatuses for positioning a body organ, and more particularly, to medical instruments that assist in manipulating and suspending a patient's heart at a desired position during diagnostic and surgical procedures.

BACKGROUND OF THE INVENTION

Coronary artery disease results in a narrowing of the coronary arteries, which are the blood vessels that supply the heart with oxygen and nutrients. There are two main coronary arteries: the left main coronary artery, which supplies blood to the left ventricle, and the right main coronary artery, which supplies blood to the right ventricle as well as the posterior surface of the left ventricle. These main coronary arteries give rise to several branches that extend into the heart muscle (myocardium), bringing vital nutrients to each muscle cell. The heart relies on these nutrients as it works constantly to pump blood through the body. Narrowing of the coronary arteries reduces blood flow to the myocardium and, if untreated, can damage and/or destroy the heart muscle.

In some cases, coronary artery disease may be treated by the use of drugs and/or by modifications in behavior and diet. For certain patients, however, a coronary artery bypass graft (CABG) procedure is the preferred form of treatment to restore adequate blood flow. A CABG procedure improves the flow of blood and ensures that the heart muscle is receiving an adequate supply of oxygen-rich blood.

In a CABG procedure, a blocked section of the artery is literally "bypassed" by attaching a healthy segment of blood vessel downstream from the diseased or blocked area. During surgery, an incision is made in the patient's chest and the sternum is divided to allow access to the pericardial sac, which envelops and protects the heart.

Some CABG procedures can be performed with a beating heart, while others require that the heart be arrested, usually by administering a chemical solution, called cardioplegia, that temporarily paralyzes the heart muscle fibers. In procedures where the heart is arrested, circulation is maintained by a heart-lung machine.

During the procedure, manual manipulation and repositioning of the heart is usually necessary to access the blocked arteries. The posterior descending artery, for example, lies on the posterior surface of the heart. The surgeon or a surgical assistant is therefore required to lift and rotate the heart to expose the artery. Often, a surgeon uses his or her own hands to position the heart. However, it is difficult to maintain the heart in a secure and proper position by such techniques. In addition, direct manual contact with the heart may impair circulation, leading to reductions in cardiac output and blood pressure. Care must be exercised to avoid trauma to the heart or pericardial sac to avoid the formation of excessive adhesions.

In order to overcome these problems, devices such as slings and balloons have been developed to help position and/or stabilize the heart. A balloon, for example, is placed underneath the heart and is thereafter inflated to lift the heart into a desired position. A sling, on the other hand, is a fabric or plastic based device that is placed around the heart in the manner of a hammock. The heart can then be positioned by moving the sling.

While attempts have been made to support the heart during a CABG surgery, the resulting devices and techniques have several drawbacks that have hindered their acceptance in the art. For example, slings made of net or fabric tend to interfere with access to the surgical target. Moreover, net slings require special techniques or procedures to remove the net from the surgical target area. Where a balloon is employed, the heart is freely slidable on the balloon, and not necessarily securely positioned, thus posing a risk of damage during the surgical procedure. Moreover, if a balloon is over-inflated, it can exert excess pressure on the heart, potentially causing damage to the heart.

In addition to the aforementioned problems, the recent trend in moving toward less invasive procedures makes placement of a sling or inflatable balloon nearly impossible. A minimally invasive cardiac surgery (MICS) procedure is a new technique which, compared with standard cardiac procedures, causes less pain, speeds recovery, and delivers identical results at less cost.

MICS procedures are usually performed on the beating heart, thereby eliminating the expense and risk of stopping the heart and the necessity of a heart-lung bypass machine. The procedure is performed by making an incision in the chest (thorocotomy). A heart stabilizer can be used to restrict movement of the heart within the limited surgical field.

Since the surgeon is operating on a beating heart, both movement and blood can cause a sling or balloon to displace during surgery. Moreover, the surgeon's ability to access and manipulate the heart is hampered since the incision used to access the thoracic cavity is much smaller. As a result, the limited surgical field makes placement of any type of inflatable balloon or sling around the heart very difficult.

Surgeons have also employed retraction sutures and retraction tapes to lift and secure the heart during surgical procedures. In one technique a number of retraction sutures (e.g., three) are placed deep within the pericardium and then tensioned to lift the heart. In another technique, retraction tapes, which are usually thick, porous straps, are placed strategically around the heart. The tapes are then gradually retracted to reposition the heart and expose the target artery. Typically, two pairs of retraction tapes are employed. The first pair is passed through the transverse sinus, and the second pair is passed beneath the inferior vena cava. One end of each tape is fixed to a stationary support and the other end of each tape is kept free. The free ends can then be retracted to position the heart. Once the heart is in the desired position, the free ends of the tapes can be secured to the support.

The use of retraction sutures and retraction tapes has some drawbacks in that it is difficult and time consuming to place these devices properly while avoiding risk of damage to the heart.

For example, when sutures are used, the tip of the suture needle must be placed along the pericardium, and then rotated to penetrate through the tissue. Unpredictable motion of the epicardial surface during needle placement may cause laceration of the heart or puncture of a coronary artery. A high degree of skill is also required to grasp the proper amount of tissue. If an insufficient amount of tissue is engaged, the suture may tear through the tissue and fail. Conversely, if too much tissue is engaged, the suture may penetrate and possibly damage an underlying organ, such as the lung.

The proper placement of retraction tapes is made difficult due to the limited surgical field and reduced field of vision. Moreover, the procedure can be time consuming and risky since a pair of retraction tapes needs to be placed through the transverse sinus. Traumatic stressing of the transverse sinus, or excessive destruction of the tissue, can lead to stenosis, further compromising the patient's health. Further, the placement of retraction tapes directly around the heart can lead to a significant drop in blood pressure.

Accordingly, there is a need for an organ positioning and manipulating device which can be easily, quickly, and safely employed to present and expose target surgical tissue.

SUMMARY OF THE INVENTION

The present invention provides a medical instrument for positioning an internal organ during surgical and diagnostic procedures. The instrument is useful in that it can be safely and effectively utilized during surgical procedures to reposition a body organ temporarily. This instrument enables the organ of interest or tissue adjacent to the organ of interest to be securely grasped, and it also enables manipulation and repositioning of the organ.

In one embodiment, the medical instrument includes a body having a tissue grasping element and an actuating member effective to move the tissue grasping element between an open position and a closed position. The instrument also includes a flexible member which has at least one free end and another end secured to the body. In use, the tissue grasping element grasps or penetrates a portion of the tissue on or near the body organ. Tension can then be applied to the flexible member to reposition and secure the body organ.

In one embodiment of the invention, the tissue grasping element includes first and second opposed tissue penetrating claws, and the actuating member includes opposed first and second actuating members. The tissue penetrating claws are opened by bringing the first and second actuating members in contact with each other.

In a further embodiment, the medical instrument includes a housing disposed on the body, and a removable applicator sleeve slidably disposed on the housing and adapted to selectively engage the actuating member. The applicator sleeve is movable between a first, proximal position in which the applicator sleeve is free from contact with the actuating member, and a second, distal position in which the applicator sleeve is able to engage the actuating member and thereby move the tissue grasping element between an open position and a closed position.

In another embodiment, the medical instrument includes a handle mated to the free end of the flexible member. The actuating member can be in the form of a wire that communicates between a portion of the handle and the tissue grasping element. A lever movably disposed on the handle and attached to the wire is effective to move the wire and thereby move the tissue grasping element between the open and closed positions. The medical instrument can optionally include a locking element, such as a latch disposed on the handle and mated to the lever for releasably locking the tissue grasping element in one of the open or closed positions.

In yet another embodiment, the medical instrument includes an elongate, rigid body having a proximal end and a distal end. The tissue grasping element extends from the distal end of the body and is mated to a cable slidably disposed on the body and connected to a lever. Movement of the lever is effective to move the tissue grasping element between the open and closed positions.

The present invention also provides a method for positioning a body organ utilizing a medical instrument according to the present invention.

BRIEF DESCRIPTION OF THE DRAWINGS

The invention will be more fully understood from the following detailed description taken in conjunction with the accompanying drawings, in which like reference numerals designate like parts throughout the various figures, and wherein.

DETAILED DESCRIPTION OF THE INVENTION

The present invention relates to a medical instrument for assisting in manipulating and suspending a body organ at a desired position during diagnostic and/or surgical procedures. The medical instrument of the present invention is particularly useful for positioning a patient's heart during a coronary artery bypass procedure. The instrument can be easily, quickly, and safely employed to present and expose target surgical tissue.

In general, the medical instrument according to the present invention includes a body having a tissue grasping element, an actuating member effective to move the tissue grasping element between an open position and a closed position, and a flexible member. In use, the actuating member is manipulated to cause the tissue grasping element to penetrate or grasp a portion of the tissue on or near the body organ of interest. The flexible member can then be tensioned and retracted to position the body organ as desired. Once the body organ is in the desired position, a free end of the flexible member can be secured to a support (not shown) to maintain the body organ in a desired position.

Figure 1:
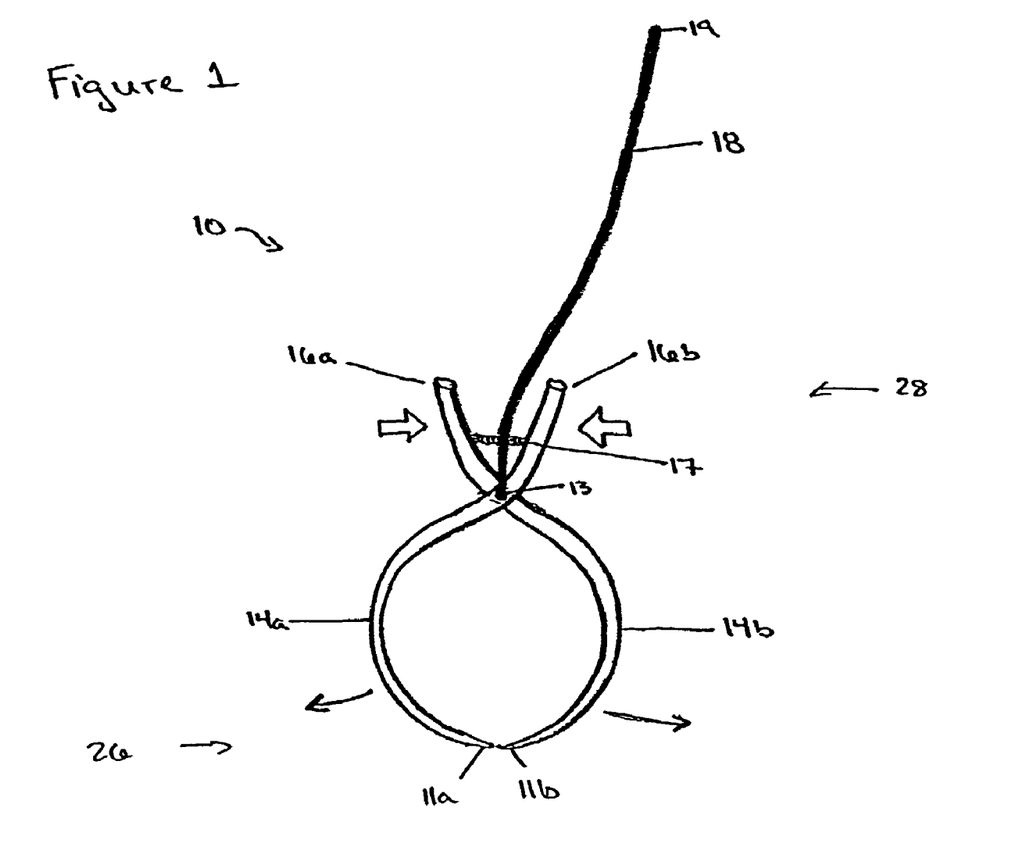
FIG. 1 is a perspective view of a medical instrument according to one embodiment of the present invention.

FIG. 1 illustrates one embodiment of a medical instrument 10 according to the present invention. In general, the medical instrument includes a body 13, a tissue grasping element 14, and an actuating member 16. The body 13 mates the tissue grasping element 14 with the actuating member 16, and can have any shape and can be any type of connector, or similar device. In one embodiment, the body 13 is a rivet or screw which forms a pivot point between the tissue grasping element 14 and the actuating member 16. Alternatively, the body 13 can be a separate element disposed around pivot point to join the tissue grasping element 14 and the actuating member 16, or it can be formed integrally with the tissue grasping element 14 and the actuating member 16.

The tissue grasping element 14 extends distally 26 from the body 13 and includes first and second opposed tissue penetrating claws 14a, 14b. The tissue grasping element 14 can be removably appended to the body 13 to optionally allow the tissue grasping element 14 to be replaced after use, or, alternatively, the tissue grasping element 14 can be integral with the body 13. The tissue penetrating claws 14a, 14b have a semi-circular shape and include two opposed tissue piercing ends 11a, 11b which meet in the closed position to essentially form a circle or oval, as shown. In use, the tissue penetrating claws 14a, 14b are movable between a closed position (shown in FIGS. 1, 2A, and 2C) and an open position (shown in FIG. 2B). While each tissue penetrating claw 14a, 14b is shown as having a generally semi-circular shape, a person having ordinary skill in the art will appreciate that the tissue penetrating claws 14a, 14b can have any shape, such as square, oval, rectangular, etc. A person having ordinary skill in the art will appreciate that the term "tissue penetrating claw" as used herein is intended to include any element, having any shape or size, that is effective to penetrate tissue.

Figures 2A, 2B:
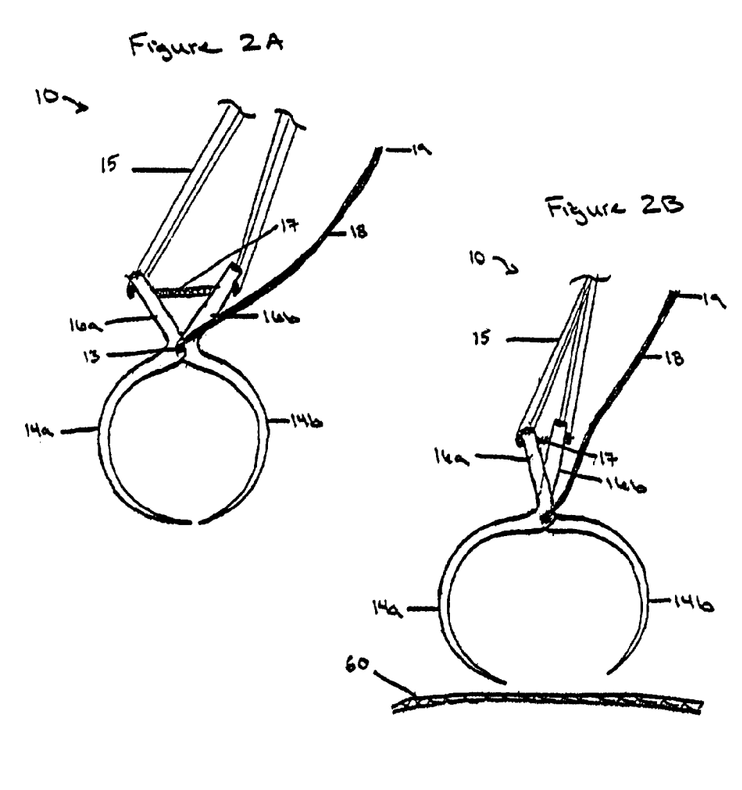
FIG. 2A is a perspective view of the medical instrument of FIG. 1 in a closed position and including a positioning tool according to the present invention.
FIG. 2B is a perspective view of the medical instrument of FIG. 1 in an open position, actuated by the positioning tool of FIG. 2A.
Figure 2C:
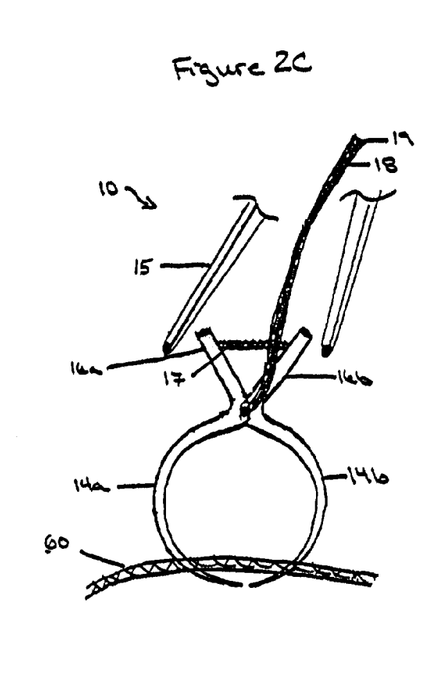
FIG. 2C is a perspective view of the medical instrument of FIG. 1 in a closed position and grasping a portion of tissue.

The first and second actuating members 16a, 16b extend proximally 28 from the body 13 and are opposed to the tissue penetrating claws 14a, 14b. The actuating members 16a, 16b are effective to move the tissue penetrating claws 14a, 14b between the open and closed positions, as shown in FIGS. 2A–2C. The actuating members 16a, 16b can be elongated handles or similar structures formed integrally with, or mated to, the tissue penetrating claws 14a, 14b. Alternatively, the actuating members 16a, 16b can extend into, attach to, or be disposed within the body 13 to mate directly or indirectly with the tissue grasping element 14. In an exemplary embodiment, actuating member 16a is integral with tissue penetrating claw 14b, and actuating member 16b is integral with tissue penetrating claw 14a. The two integral members can be connected at the pivot point formed by the body 13.

The medical instrument 10 can optionally include a biasing element 17 to maintain the tissue penetrating claws 14a, 14b in one of the open or closed positions. The biasing element 17 can be a spring, or similar device, mated to the actuating members 16a, 16b or to the tissue penetrating claws 14a, 14b. Alternatively, the biasing element 17 can be mated to, or formed integrally with, the body 13.

In use, the biasing element 17 applies a force to maintain the tissue penetrating claws 14a, 14b in one of the open or closed positions. The force of the biasing element 17 can be overcome by grasping the actuating members 16a, 16b causing the members to contact each other and thereby move the tissue penetrating claws 14a, 14b from the closed position, as shown in FIG. 2A, to the open position, as shown in FIG. 2B.

As shown in FIGS. 2A–2C, an instrument 15, such as forceps, may be used to apply a force to the actuating members 16a, 16b sufficient to overcome the biasing force.

Once the tissue penetrating claws 14a, 14b are in the open position, the instrument 10 can be manipulated and positioned to allow to claws 14a, 14b to penetrate tissue 60. Upon release of the actuating members 16a, 16b, the biasing element 17 causes the tissue penetrating claws 14a, 14b to return to the closed position to grasp a desired portion of tissue, as shown in FIG. 2C.

Once the tissue is firmly grasped by the medical instrument 10, the flexible member 18 can be used to retract and position the body organ. The flexible member 18 includes a proximal, free end 19 that is selectively fastenable to a support (not shown), and a distal end mated to the body 13, or any other part of the medical instrument 10. A rivet, screw, snap, buckle, adhesive, or similar attachment member can be used to secure the flexible member 18 to the body 13. Similarly, the free end 19 of the flexible member 18 can include a snap, buckle, hook and eye closure, or similar device for tying or securing the flexible member 18 to a support. The length of the flexible member 18 should be sufficient enough to allow the flexible member 18 to extend from the body organ to the support or some other position outside the body. In use, tension is applied to the flexible member 18 to retract and position the body organ (or tissue). The free end 19 of the flexible member 18 can then be secured to a support (not shown) to maintain the organ (or tissue) in a desired position.

Figure 3:
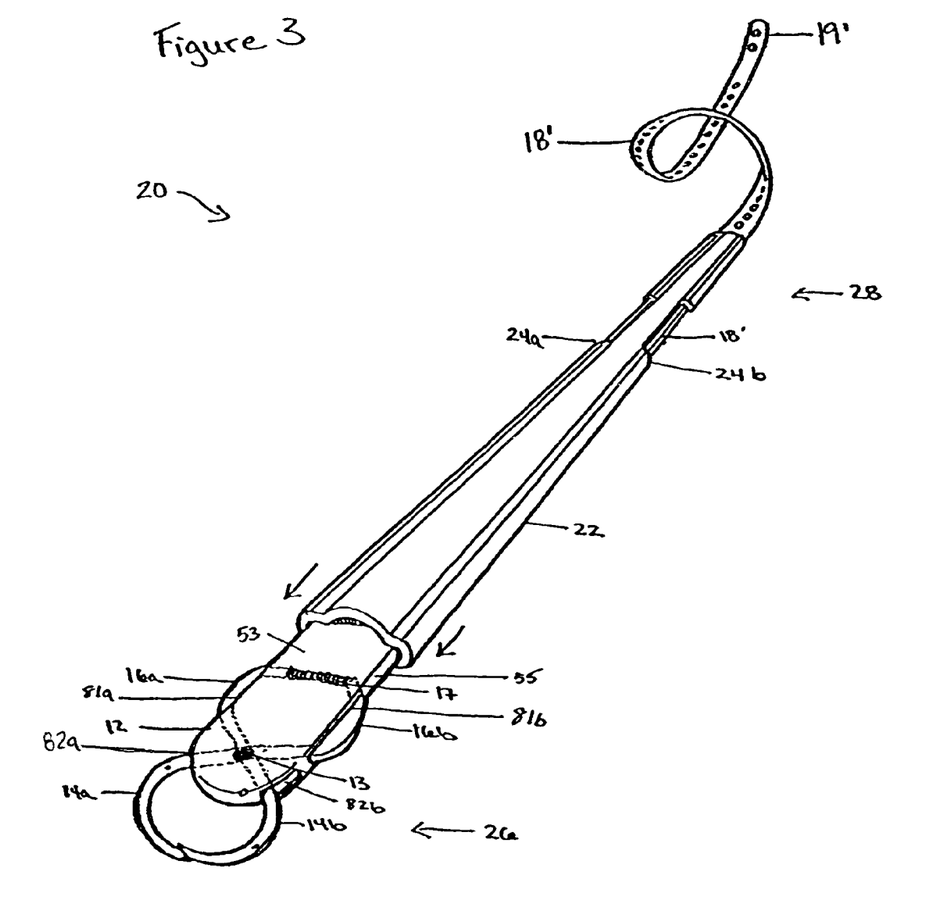
FIG. 3 is a perspective view of a further embodiment of the medical instrument of FIG. 1 including a housing and an applicator sleeve according to another embodiment of the present invention.

A further embodiment of medical instrument 10 is shown in FIG. 3, which illustrates a medical instrument 20 having a housing or body 12 disposed around medical instrument 10, a flexible member 18', and a removable applicator sleeve 22 slidably disposed on the housing 12 and the flexible member 18'. The body 13 and tissue grasping element 14 of medical instrument 10 are substantially the same as that discussed with respect to FIG. 1. The actuating members 16a, 16b, however, each may be essentially semi-circular to form a circle when the members 16a, 16b are grasped and squeezed together.

The housing 12 of medical instrument 20 is generally elongate and includes a first surface 53, a second surface (not shown) opposed to the first surface, and side surfaces 55 connecting the first and second surfaces. The first, second, and side surfaces 53, 55 define a cavity for receiving medical instrument 10. The side surface 55 includes two opposed proximal openings 81a, 81b from which the actuating members 16a, 16b of medical instrument 10 extend, and two opposed distal openings 82a, 82b from which the tissue penetrating claws 14a, 14b of medical instrument 10 extend. The proximal openings 81a, 81b should have a size substantially the same as the length of the members 16a, 16b so as to allow a portion of the actuating members 16a, 16b to extend therefrom. The distal openings 82a, 82b, on the other hand, should be of a sufficient size to allow the tissue penetrating claws 14a, 14b to move between th en and closed positions, respectively. Preferably, the distal openings each have a length of between about 3 to 8 mm. The size of the housing or body 12 should be sufficient to hold the medical instrument 10 therein, and should have a width less than the width of the actuating members 16a, 16b to allow the actuating members 16a, 16b to protrude there from.

One of ordinary skill in the art will appreciate that actuating members 16a, 16b need not extend from openings 81a, 81b. Instead, a structure, such as a button (not shown) may extend from each opening. Force applied to the buttons will be transferred to the actuating members 16a, 16b to cause opening or closing of the tissue penetrating claws 14a, 14b.

Medical instrument 10 can be mated to, or merely disposed within, the housing or body 12. For example, the actuating members 16a, 16b and the tissue grasping element 14 can be molded into the housing 12, or they can be pivotably attached to the housing 12 with a securing device, such as with the body 13, which may be in the form of a rivet or screw as described above with respect to FIG. 1. Thus, the body 13 can extend through the first surface 53 of the housing 12, the tissue grasping element 14 and actuating member 16, and the second surface of the housing. A rivet, screw, rod, or similar attachment device can be used secure the actuating members 16a, 16b and the tissue grasping element 14 to the housing 12.

The flexible member 18' is similar in placement and operation to that described with respect to FIG. 1, however, the distal end (not shown) of flexible member 18' can be mated to the housing 12, rather than the body 13. The proximal end 19' of the flexible member 18', as well as the proximal end 28 of the applicator sleeve 22, can have a shape and size adapted to provide an improved gripping surface, and to allow the medical instrument 20 to be secured to a support (not shown). In use, the flexible member 18' is disposed within the applicator sleeve 22 to allow the applicator sleeve 22 to slidably move with respect to the housing 12.

The applicator sleeve 22 has a substantially rigid elongate body and it is effective to depress the actuating members 16a, 16b, and thereby move the tissue grasping element 14 to the open position. The applicator sleeve 22 includes an inner cavity which can be dimensioned to fit slidably over the housing 12 and the flexible member 18'. The sides of the applicator sleeve 22 should conform to the sides of the housing 12, such that movement of the applicator sleeve 22 over the housing 12 will depress the actuating members 16a, 16b. The proximal end 28 of the applicator sleeve 22 can include one or more openings 24a, 24b to enable a portion of the flexible member 18' to be grasped with respect to the sleeve 22, thereby preventing movement of the applicator sleeve 22. The length and width of the applicator sleeve 22 can vary depending on the size of the housing 12. In one embodiment, the applicator sleeve preferably has a length of 15 cm and a width of 15 mm.

Figure 4A:
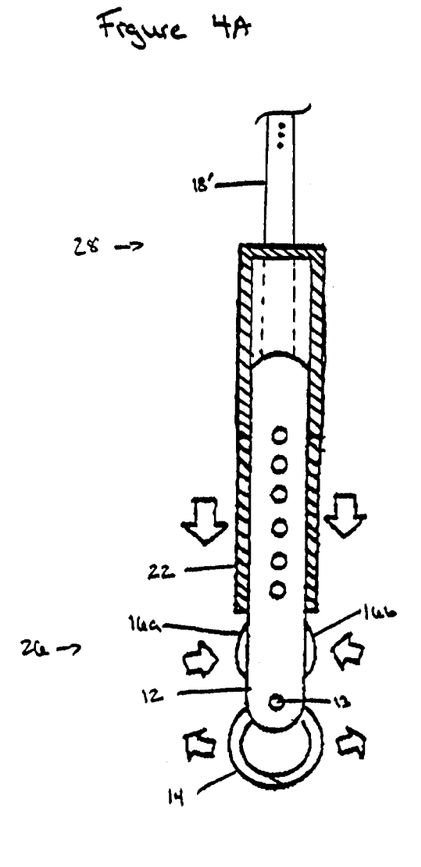
FIG. 4A is a perspective view of a medical instrument similar to that of FIG. 3 in a closed position.
Figure 4B:
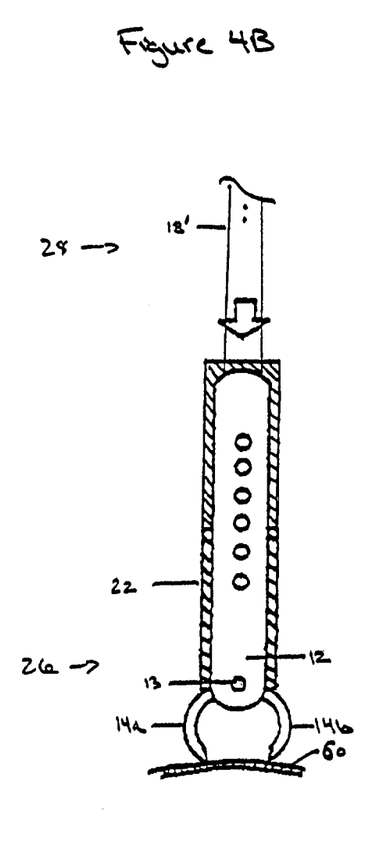
FIG. 4B is a perspective view of the medical instrument of FIG. 4A in an open position, actuated by an applicator sleeve.
Figure 4C:
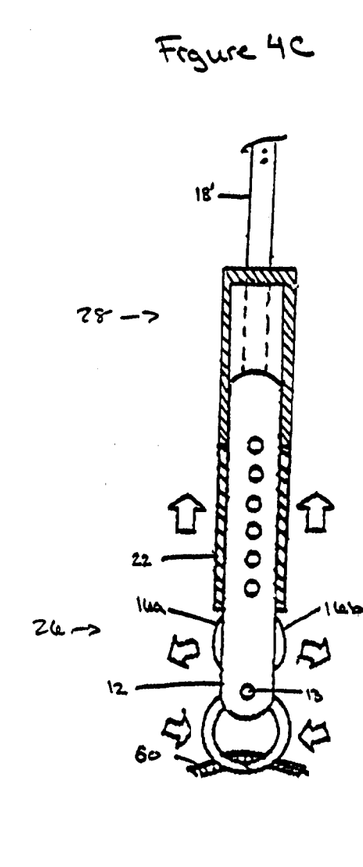
FIG. 4C is a perspective view of the medical instrument of FIG. 4A in a closed position and grasping a portion of tissue.

As shown in FIGS. 4A–4C, the applicator sleeve 22 is movable between a first, proximal position 28 (shown in FIG. 4A), and a second distal position 26 (shown in FIG. 4B). In the first, proximal position 28, the applicator sleeve 22 is free from contact with the actuating members 16a, 16b. In the second, distal position 26, on the other hand, the applicator sleeve 22 is able to engage the actuating members 16a, 16b causing them to move together, thus moving the tissue penetrating claws 14a, 14b from the closed (shown in FIG. 4A) to the open position (shown in FIG. 4B). Once the sleeve 22 is returned to the proximal position 28 (shown in FIG. 4C), the claws 14a, 14b close together and engage the tissue 50.

In one embodiment, the flexible member 18' is pulled through the inner lumen of the applicator sleeve 22 and held with tension to secure the applicator sleeve 22 onto the housing 12. The applicator sleeve 22 is then used to manipulate the body 12 and cause the tissue grasping element 14 to grasp or penetrate tissue 60. The flexible member 18' can then be released and the applicator sleeve 22 slid off of the body 12. Tension can then be applied to flexible member 18' to retract and position the body organ (or tissue). The free end 19' of the flexible member 18' can then be secured to a support (not shown) to maintain the organ (or tissue) in a desired position.

Another embodiment of a medical instrument 30 is illustrated in FIGS. 5–7B and includes a body 37, a tissue grasping element 31, a handle 32, a flexible member 39 disposed between the body 37 and the handle 32, and an actuating system. The body 37 can have any shape, but is preferably substantially disk-shaped and includes an inner cavity or lumen 35 for receiving the tissue grasping element 31. The cavity 35 should have a shape that allows the tissue grasping element to slidably move therein, but yet prevents wobbling of the tissue grasping element during use. The distal end 26 of the body 37 can include an indented or concave portion 83 and an opening 45 from which the tissue grasping element 31 extends. The opening 45 can have any shape, and should have a size sufficient to allow the tissue grasping element 31 to protrude there from. When the tissue grasping element is actuated, and thereby extended from the opening 45, the concave portion 83 allows the tissue grasping element 31 to extend beyond the distal end 26 of the body 37 and grasp a desired portion of tissue. The body 37 can also include a proximal opening 47 for receiving and/or mating with the flexible elongate member 39 and the actuating member 41. The body 37 can be made from the same materials as housing 12 discussed with respect to FIG. 3.

Figure 5:
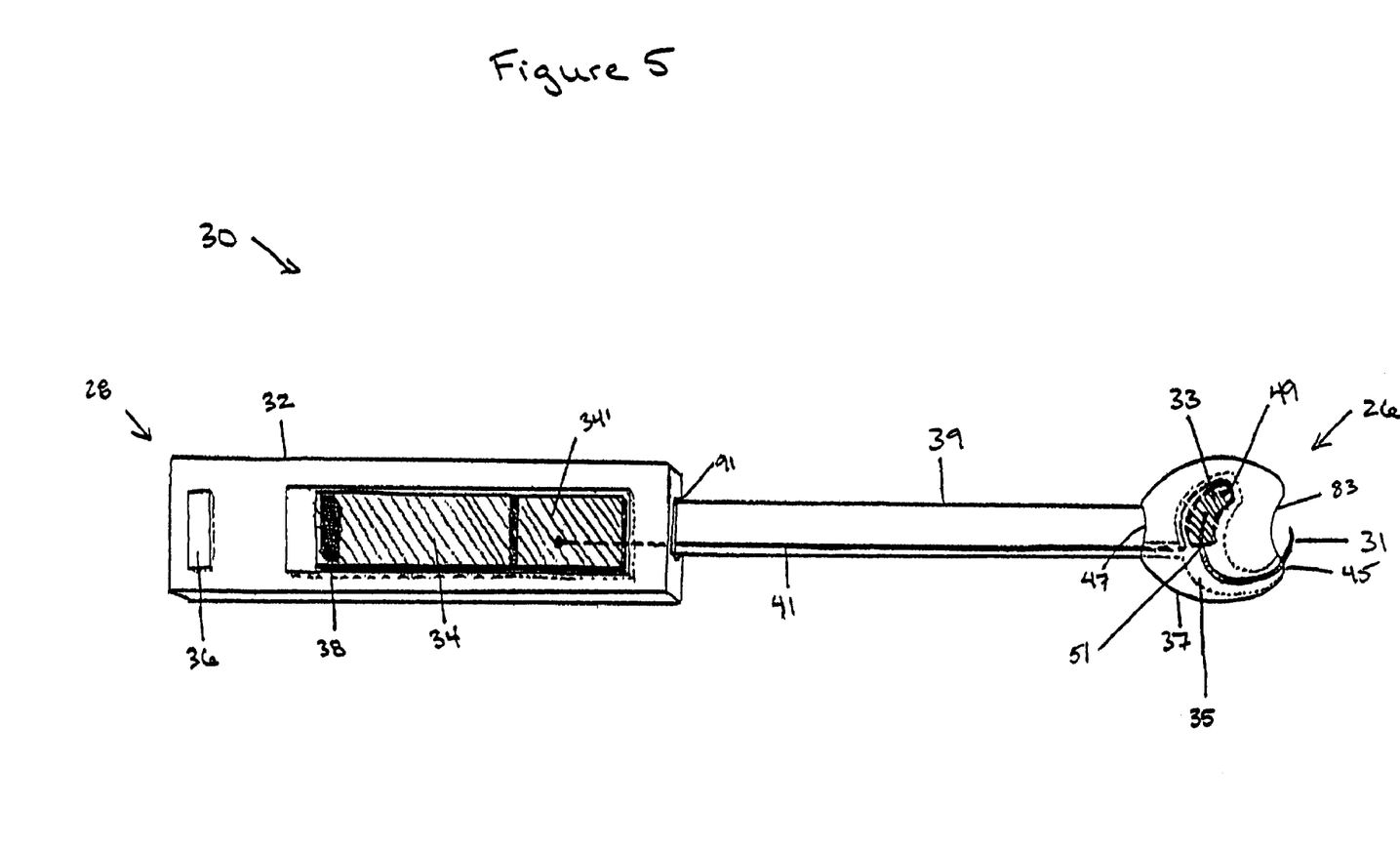
FIG. 5 is a perspective view of a medical instrument according to yet another embodiment of the present invention.

The tissue grasping element 31 is disposed within the cavity 35 of the body 37, and is slidably movable between a closed position, in which a portion of the tissue grasping element 31 extends from the opening 45 in the distal end 26 of the body 37, and an open position, in which the tissue grasping element 31 is fully disposed within the body (not shown). The tissue grasping element can be substantially semi-circular and can be made from a needle, or similar tissue penetrating member. The materials used to construct the tissue grasping element can be the same or similar materials as tissue grasping element 14, discussed with respect to FIG. 1.

The flexible member 39 is effective to mate the body 37 to the handle 32, and it includes a distal end mated to or disposed within the body 37 at opening 47, and a proximal end mated to the handle 32. The flexible member 39 is similar to flexible members 18 and 18' described with respect to FIGS. 1 and 3, and should have a length sufficient to allow the handle 32 to be positioned at a location outside of the body. In an exemplary embodiment, a path or lumen is formed on or within the flexible member for receiving and/or guiding a wire 41, which is part of the actuating system. The flexible member 39 can be semi-rigid, or alternatively, the medical instrument 30 can optionally include a second flexible member (not shown) for providing added rigidity to the flexible member 39, and for providing additional stability between the body 37 and the handle 32. The distal end 26 of the second flexible member can be removably disposed within the opening 47 of the body 37 to allow the second flexible member to be removed once the organ is positioned.

The actuating system used with medical instrument 30 includes a rotatable member 33 disposed within the body 37, a lever 34 disposed on the handle 32, and a wire 41 connecting the rotatable member 33 to the lever 34. The actuating system can also include a biasing element 43 for maintaining the tissue grasping element 31 in one of the open or closed positions.

The rotatable member 33 is disposed with the cavity 35 of the body 37 and is slidably movable along a groove or guide path defined by the cavity 35. A first end 51 of the rotatable member 33 is mated to the proximal end 28 of the tissue grasping element 31, and a second end 49 of the rotatable member 33 is mated to the wire 41, which extends along the flexible member 39 to the lever 34 on the handle 32. The rotatable member can have any shape, and should be sized to fit within the cavity 35. Movement of the actuating member 41 is effective to move the rotatable member 33 and thereby move the tissue grasping element 31 between the open and closed positions.

The wire 41 (or a similar element), disposed within or along the flexible member 39, is able to effect movement of the rotatable member between the open and closed positions. The distal end 26 of the wire 41 is mated to the rotatable member 33, and the proximal end 28 of the wire is mated to a lever 34 that is disposed within the handle 32. A rivet, screw, snap, adhesive, or similar attachment member can be used to secure the wire 41 to the rotatable member 33 and the lever 34. In use, movement of the lever 34 is effective to move the wire 41, thereby moving the rotatable member 33 and the tissue grasping element 31 between an open (retracted) position and closed (extended) position.

Figure 6:
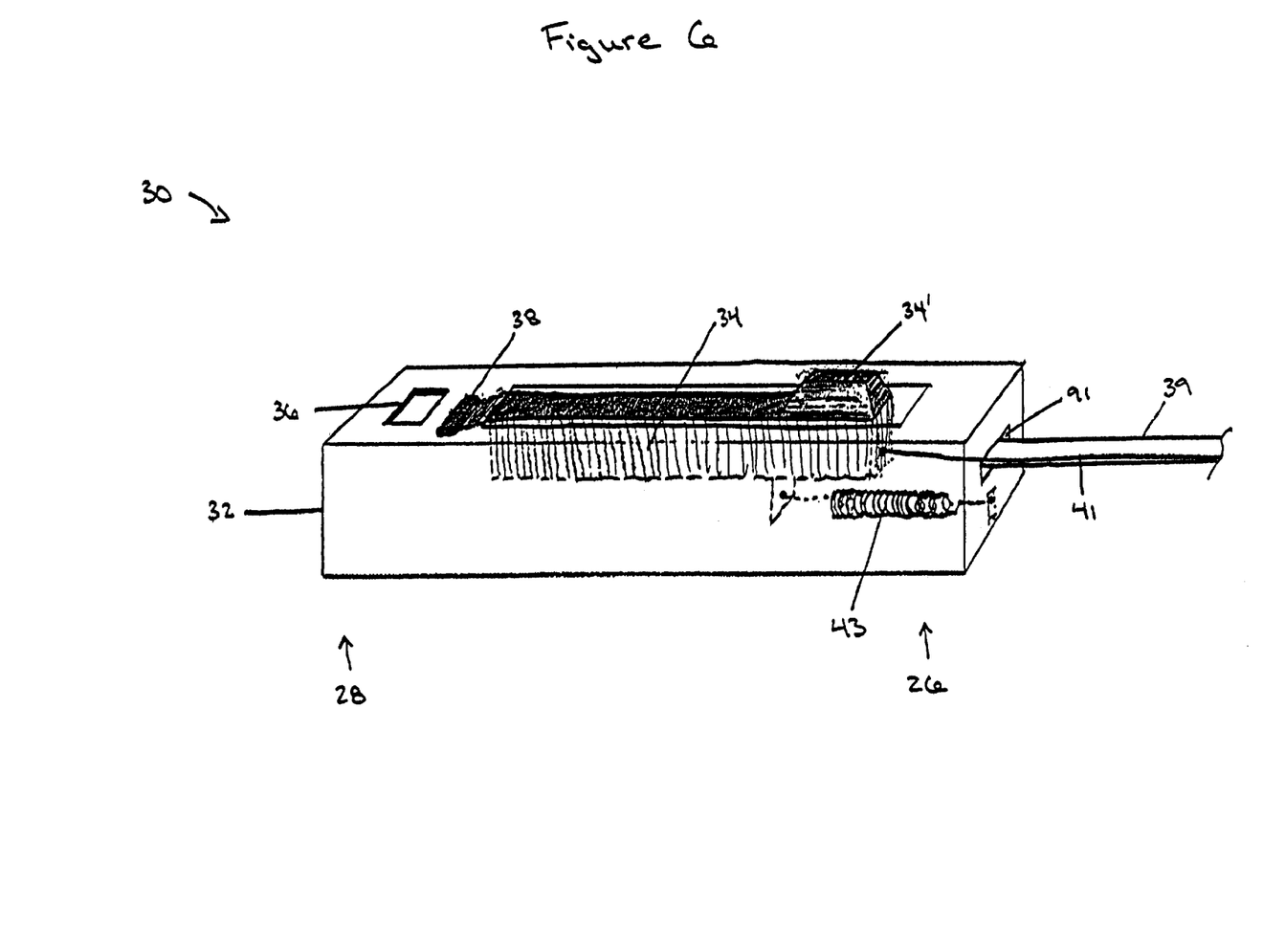
FIG. 6 is a diagram illustrating the handle of the medical instrument of FIG. 5.

The handle 32, which is shown in more detail in FIG. 6, can be constructed from any type of rigid or semi-rigid material having any shape, such as rectangular, or cylindrical, and includes an inner cavity for holding the lever 34, and optionally a locking mechanism 38 and a biasing element 43. One side (e.g., the top side) of the handle 32 includes an opening that extends between the distal and proximal ends 26, 28 of the handle 32 for receiving the lever 34. The opening should have a length sufficient to allow the lever 34 to move proximally and distally to fully open or close the tissue grasping element. The handle 32 also includes a distal opening 91 for receiving the flexible member 39 and the wire 41. The flexible member 39 can be removably disposed within opening 39, or it can be mated to the handle at or near opening 39. Optionally, the handle 32 can include a proximal opening 36 for receiving the locking mechanism, or latch 38, to lock the lever 34 in a proximal position (shown in FIG. 7B).

The lever 34 shown in FIG. 6 is disposed within the inner cavity of the handle 32 and includes a protruding portion 34' for grasping and moving the lever 34 in the proximal 28 and distal 26 directions. The lever 34 can have a variety of different shapes, but should be sized to slidably fit within the opening in the top side of the handle 32. The protruding portion 34' of the lever 34 should have a size and shape which allows a user to grasp and easily move the lever 34 along the opening in the handle 32.

Figure 7A:
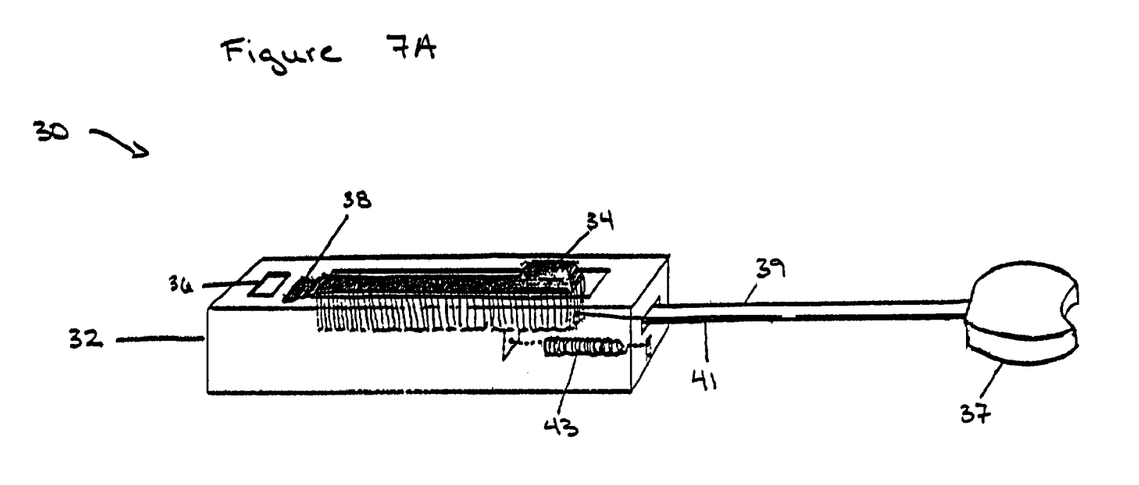
FIG. 7A is a diagram illustrating the medical instrument of FIG. 5 in an open position.
Figure 7B:
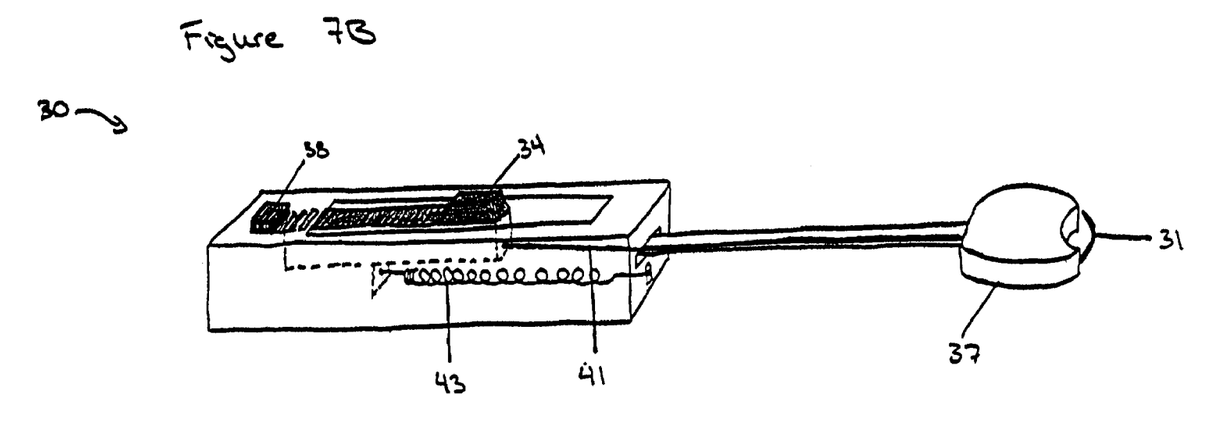
FIG. 7B is a diagram illustrating the medical instrument of FIG. 5 in a closed position.

The proximal end 28 of the lever can include a latch 38 for releasably locking the lever 34 is the proximal position (shown in FIG. 7B). The latch 38 can be attached to the proximal end 28 of the lever 34, such that movement of the lever 34 is effective to move the latch 38. When the lever 34 is in the distal position, as shown in FIG. 7A, the latch 38 is fully disposed within the handle 32. Conversely, when the lever 34 is moved to the proximal position, the latch 38 extends up into the opening 36, as shown in FIG. 7B. Pressure exerted on the latch 38 can be used to release the latch 38 from the locked, proximal position.

Medical instrument 30 can optionally include a biasing member 43, e.g. a spring, mated to the lever 34 for biasing the lever 34 to the distal 26 position, and thereby holding the tissue grasping element 31 in one of the open or closed positions. The spring 17 can be disposed within the handle 32 and attached on one end to the handle 32 and on the other end to a portion of the lever 34. The biasing member provides a force such that movement of the lever 34 in the proximal direction 28 requires a force sufficient to overcome the force of the biasing member 43. In an exemplary embodiment, the tissue grasping element 14 is biased to the open position (shown in FIG. 7A), in which the tissue grasping element 14 is fully disposed within the inner lumen of the body 37.

In use, the concave portion 83 of the body 37 is placed against a body organ (not shown), and the lever 34 is moved in the proximal direction 28, thereby pulling the wire 41 and the rotatable member 33, and causing the tissue grasping element 31 to penetrate a desired portion of tissue. Simultaneously, the latch 38 extends into opening 36 to lock the lever 34 in the proximal position and the tissue grasping element 31 in the closed (extended) position. The handle 32 can then be tensioned and retracted to position the body organ. The weight of the handle 32 can be used to lay the handle 34 at a position outside of the human body to maintain the body organ in the desired position. Where the medical instrument 30 includes a second flexible member, the distal end 26 of the second flexible member can be removed from opening 47 in the body 37 to allow flexible member 39 to bend. This features provides ease of placement of the handle at any location outside of the human body.

Figure 8:
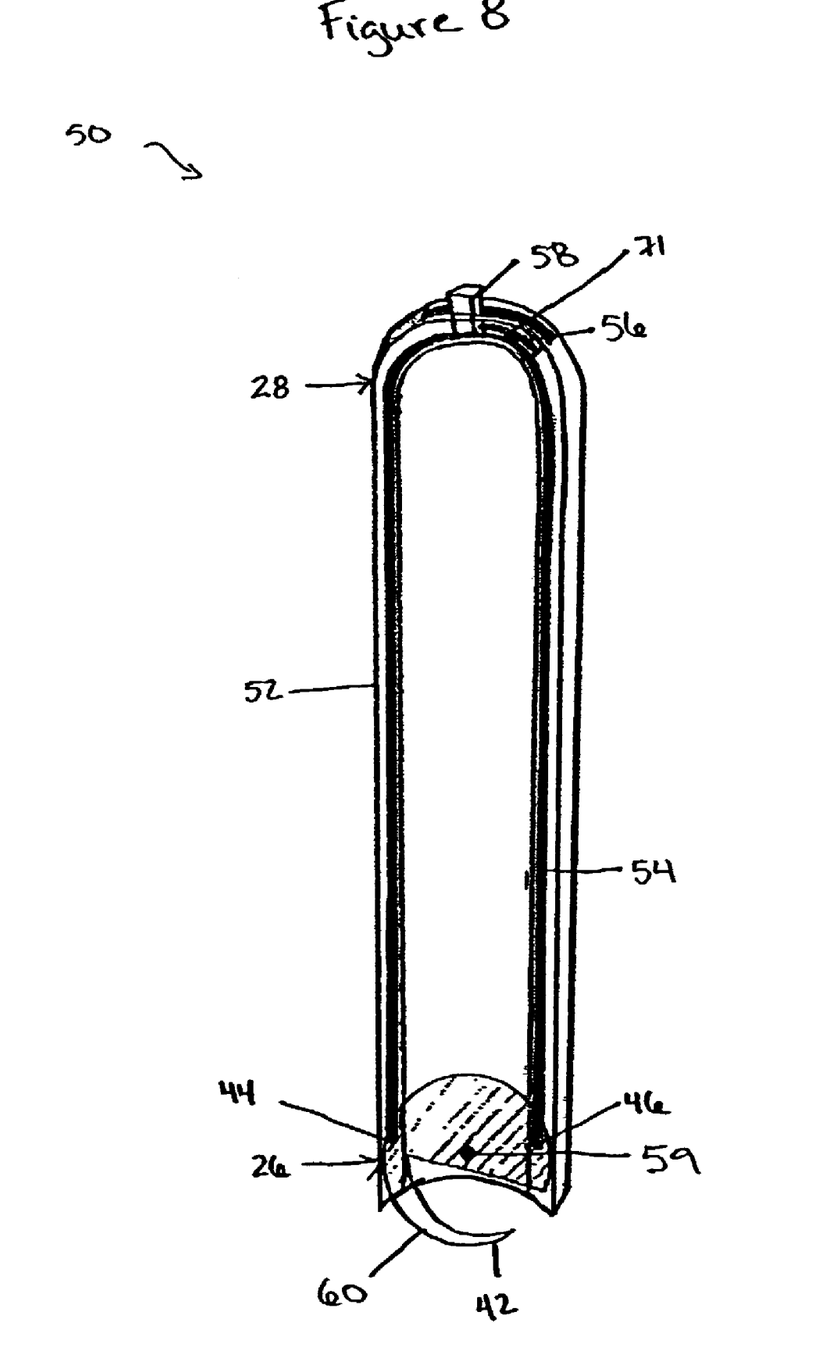
FIG. 8 is a perspective view of a medical instrument according to another embodiment of the present invention.

FIG. 8 illustrates another embodiment of a medical instrument 50 including an elongate, rigid or semi-rigid body 52 which defines a cavity for receiving a tissue grasping element 60. The body 52 includes a proximal end 28 having an opening or slit 56 for receiving a lever 58 effective to move an actuating member 54, and an open distal end 26 which is adapted to receive the tissue grasping element 60. The cavity of the body 52 can extend throughout the length of the body, or can be formed within the distal end 26 of the body. The outer periphery of the body 52 includes a groove or lumen for receiving the actuating member 54. In use, the body can act as a flexible elongate member for positioning an organ, or alternatively, a flexible elongate member (not shown) similar to flexible elongate members 18, 18' can extend from the proximal end of the medical instrument 50.

The tissue grasping element 60 is a substantially diskshaped member that includes a tissue piercing portion 42 extending from the open distal end 26 of the body 52. In one embodiment, shown in FIG. 8, the tissue grasping element 60 is pivotably mated to the body 52 at pivot point 59 located substantially at the center of the diskshaped tissue grasping element 60. The actuating member, e.g. a cable or wire 54 is attached to the tissue grasping element 60 at two opposed points 44, 46. The points 44, 46 should be located at opposed points adjacent the tissue piercing portion 42. In an alternative embodiment (not shown), the wire 54 can be attached to the tissue grasping element 60 at a single point 44 or 46. In use, movement of the wire 54 is effective to rotate the tissue grasping element 60, thereby causing the tissue piercing portion 42 to extend and retract the from the opening in the distal end 26 of the body 52.

The wire 54 is slidably disposed on the body 52 along or within the groove or lumen around the peripheral edge of the body 52, and mates the tissue grasping element 60 and the lever 58. The wire 54 can extend from one point 44 to the lever 58, and then connect to the tissue grasping element 60 at opposed point 46. Alternatively, the wire 54 can be attached to the tissue grasping element 60 at one point 44 or 46 and terminate at the lever 58.

The lever 58 is effective to apply a force to the wire 54 to move the tissue grasping element 60 between the open and closed positions. The lever 58 can be any type of structure, such as a handle, which slidably extends from the slit or opening 56 in the body. While the lever 58 is shown extending from slit 56 at the proximal end 28 of the body 52, the lever 58 and the slit 56 can be positioned at any location on the body 52.

The medical instrument 50 can optionally include a biasing element, e.g. a spring 71, to bias the lever 58 to hold the tissue grasping element 60 in one of the open or closed positions. Alternatively, the spring 71 can bias the tissue grasping element 60 (not shown).

While FIG. 8 illustrates a pulley system for rotating the tissue grasping element 60, a person having ordinary skill in the art will appreciate that other systems can be used to actuate the tissue grasping element 60. By way of non-limiting example, a gear can be disposed within the body 52 for turning the tissue grasping element 60.

The body 13, 37, 52 of the medical instrument 10, 20, 30, 50 according to the present invention can be formed from a medically compatible rigid or semi-rigid material. Suitable materials include plastics, light weight metals or metal alloys, and composite materials. Preferably, the body 13, 37, 52 is made of a biocompatible material, such as, for example, titanium or a titanium alloy, or a variety of rigid polymers known to be useful in medical devices. Similarly, in certain embodiments of the invention, other parts of the medical instrument 10, 20, 30, 50, such as the housing 12, applicator sleeve 22, handle 32, lever 34, 58, and rotatable member 33, can be made from the same or similar material as the body 13, 37, 52.

The tissue grasping element 14, 31 60 can be made from a rigid or semi-rigid material, such as plastic, light weight metal or metal alloy, or a composite material. Preferably, the tissue grasping element is made from stainless steel. Any standard size needle can be used to form the tissue grasping element 14. However, the tissue grasping element 14 is preferably an SH½ circular needle, a CT2 needle, or a V-7 needle.

Structures from which the flexible member 18, 18', 39 can be made include straps, cords, sutures, and bands. A variety of suitable materials can be used to form the flexible member 18, including any material that is substantially inelastic and/or flexible. Alternatively, the flexible member 18, 18', 39 can be made from an elastic material, such as latex or silicone.

In use, medical instrument 10, 20, 30, 50 is effective for positioning any body organ, but is preferably used for positioning a patient's heart. The procedure involves positioning the body in proximity to the internal organ to be repositioned, and then manipulating the body so that the tissue grasping element grasps or penetrates a desired portion of tissue. Tension can then be applied to the flexible member to reposition and secure the body organ. Once the organ is properly positioned, the free end of the flexible member can be secured to a support.

Those having ordinary skill in the art will know, or be able to ascertain, using no more than routine experimentation, many equivalents to the specific embodiments of the invention described herein. These and all other equivalents are intended to be encompassed by the following claims. All publications and references cited herein including those in the background section are expressly incorporated herein by reference in their entirety.

What is claimed is:

1. A medical instrument effective to assist in positioning an internal organ during a surgical procedure, comprising:
a housing;
a tissue gasping element appended to the housing and having first and second opposed tissue penetrating claws selectively movable about a pivot point between an open position and a closed position, the first and second opposed tissue penetrating claws being biased to one of the open and closed positions, and being configured to penetrate tissue while moving from the open position to the closed position;
first and second opposed actuating members mated to the housing and effective to move the tissue grasping element between the open and closed positions, each actuating member extending from an opening formed in the housing;
a biasing element extending between the first and second opposed actuating members in house housing and adapted to bias the first and second tissue penetrating claws to one of the open arid closed positions; and
a flexible member having a portion secured to the housing and at least one free end that is selectively fastenable to a support.

2. The medical instrument of claim 1, wherein a force applied to bring the first and second opposed actuating members in contact with each other causes opening of the tissue penetrating claws.

3. The medical instrument of claim 2, wherein the first and second tissue penetrating claws are biased to the closed position.

4. The medical instrument of claim 1, wherein the tissue grasping element forms substantially a circular shape in the closed position.

5. The medical instrument of claim 1, wherein the flexible member is selected from the group consisting of a strap, a band, a tape, and a sting.

6. The medical instrument of claim 1, wherein the housing is elongate and the device further comprises a removable applicator sleeve slidably disposed on the housing and adapted to selectively engage the first and second opposed actuating members.

7. The medical instrument of claim 6, wherein the applicator sleeve is movable between a first, proximal position in which the applicator sleeve is free from contact with the first and second opposed actuating members, and a second, distal position in which the applicator sleeve is able to engage the first and second opposed actuating members and thereby move the tissue grasping element between the open and closed positions.

8. The medical instrument of claim 7, wherein the tissue grasping element is disposed on the distal end of the housing.

9. The medical instrument of claim 7, wherein the first and second tissue penetrating claws are biased to the closed position.

10. The medical instrument of claim 7, wherein at least a portion of the applicator sleeve defines an inner lumen.

11. The medical instrument of claim 10, wherein the inner lumen is adapted to receive at least a portion of the flexible member.

12. The medical instrument of claim 11, wherein the flexible member is selected from the group consisting of a strap, a band, a tape, and a string.

13. A method for positioning a body organ, comprising:
providing a medical instrument having
a body,
a tissue grasping element appended to the body and having first and second opposed tissue penetrating claws selectively movable between an open position and a closed position, the first and second opposed tissue penetrating claws being biased to one of the open and closed positions, and being configured to penetrate tissue while moving from the open position to the closed position an actuating member mated to the body and effective to move the tissue grasping element between the open and closed positions, and a flexible member having a portion secured to the body and at least one free end that is selectively fastenable to a support;

positioning the body in proximity to an internal organ to be repositioned;

manipulating the body so that the tissue grasping element grasps a desired portion of tissue; and applying tension to the flexible member to reposition and secure the body organ.

14. A medical instrument effective to assist in positioning an internal organ during a surgical procedure, comprising:

an elongate body;

a tissue gasping element appended to the body and having first and second opposed tissue penetrating claws selectively movable between an open position and a closed position, the first and second opposed tissue penetrating claws being biased to one of the open and closed positions, and being configured to penetrate tissue while moving from the open position to the closed position;

an actuating member comprising first and second opposed members, each member extending through an opening formed in the body and effective to move the tissue grasping element between the open and closed position;

a flexible member having a portion secured to the body and at least one free end that is selectively fastenable to a support; and a removable applicator sleeve slidably disposed on the body and adapted to selectively engage the actuating menber.

15. The medical instrument of claim 14, wherein the applicator sleeve is movable between a first proximal position in which the applicator sleeve is free from contact with the actuating member, and a second, distal position in which the applicator sleeve is able to engage the actuating member and thereby move the tissue grasping element between the open and closed positions.

16. The medical instrument of claim 14, wherein the tissue grasping element is disposed on the distal end of the body.

17. The medical instrument of claim 16, wherein the tissue grasping element comprises first and second opposed tissue penetrating claws.

18. The medical instrument of claim 17, wherein the first and second tissue penetrating claws are biased to the closed position.

19. The medical instrument of claim 14, wherein at least a portion of the applicator sleeve defines an inner lumen.

20. The medical instrument of claim 19, wherein the inner lumen is adapted to receive at least a portion of the flexible member.

21. The medical instrument of claim 20, wherein the flexible member is selected from the group consisting of a strap, a band, a tape, and a string.

* * * * *